(12) United States Patent
Dai et al.

(10) Patent No.: US 6,873,354 B2
(45) Date of Patent: Mar. 29, 2005

(54) SYSTEM AND METHOD FOR REGISTERING COMPLEX IMAGES

(75) Inventors: X. Long Dai, Round Rock, TX (US); Martin A. Hunt, Austin, TX (US); Bichuan Shen, Austin, TX (US)

(73) Assignee: nLine Corporation, Austin, TX (US)

( * ) Notice: Subject to any disclaimer, the term of this patent is extended or adjusted under 35 U.S.C. 154(b) by 163 days.

(21) Appl. No.: 09/949,423

(22) Filed: Sep. 7, 2001

(65) Prior Publication Data

US 2004/0174437 A1 Sep. 9, 2004

(51) Int. Cl.[7] ................................................ H04N 9/47
(52) U.S. Cl. ....................................................... 348/95
(58) Field of Search ................................ 382/141, 145, 382/151; 356/237.1, 237.2, 237.3; 348/86, 94, 95

(56) References Cited

U.S. PATENT DOCUMENTS

| | | | |
|---|---|---|---|
| 3,697,149 A | 10/1972 | Van Heeckeren et al. | ... 350/3.5 |
| 4,768,881 A | 9/1988 | Juptner et al. | ............... 356/347 |
| 5,112,129 A | 5/1992 | Davidson et al. | ........... 356/359 |
| 5,295,200 A * | 3/1994 | Boyer | .......................... 382/43 |
| 5,479,257 A | 12/1995 | Hashimoto | ................... 356/347 |
| 5,553,157 A | 9/1996 | Bourguignon et al. | ...... 382/131 |
| 5,808,735 A | 9/1998 | Lee et al. | .................... 356/237 |
| 6,078,392 A * | 6/2000 | Thomas et al. | .............. 356/457 |

FOREIGN PATENT DOCUMENTS

| | | | |
|---|---|---|---|
| EP | 0 659 021 A2 | 6/1995 | ............ H04N/7/26 |
| EP | 1 058 111 A3 | 5/2001 | .......... G01N/21/89 |

OTHER PUBLICATIONS

B. Srinivasa Reddy et al., "An FFT–Based Technique for Translation, Rotation, and Scale–Invariant Image Registration," IEEE Transactions on Image Processing, vol. 5, No. 8, XP 000595725, 6 pages.*

PCT International Preliminary Examination Report for International Application No. PCT/US02/28302 filed Sep. 6, 2002. 5 pages, mailing Apr. 14, 2004.

International Search Report for PCT/US 02/28302 8 pages, mailed Dec. 27, 2002.

Giovanna Rizzo et al., "Multimodality Biomedical Image Integration: Use of a Cross–Correlation Technique", Annual Int'l Conf. of the IEEE Engineering in Medicine and Biology Society. vol. 13, No. 1, p. 219–p. 220, published Oct. 31, 1991.

B. Srinivasa Reddy et al., "An FFT–Based Technique for Translation, Rotation, and Scale–Invariant Image Registration", IEEE Transactions on Image Processing, vol. 5, No. 8, XP 000595725, 6 pages, Aug. 1996.

PCT Written Opinion for International Application No. PCT/US02/28302 filed Sep. 6, 2002. 6 pages, mailing Jul. 23, 2003.

* cited by examiner

Primary Examiner—Wendy R. Garber
Assistant Examiner—Rashawn N. Tillery
(74) Attorney, Agent, or Firm—Baker Botts L.L.P.

(57) ABSTRACT

A system and method are described for an image registration system and method including a registration engine that receives complex image data for corresponding images. The registration engine generates a correlation map between the complex image pair for relative translation by calculating an inverse of the complex conjugate product of the frequency data of the first image and the frequency domain data of the second, corresponding, image. The frequency domain data may be obtained using Fast Fourier transform-based techniques.

17 Claims, 2 Drawing Sheets

SYSTEM AND METHOD FOR REGISTERING COMPLEX IMAGES

TECHNICAL FIELD

The following invention relates in general to the field of imaging and inspection systems and more particularly to an image registration system and method.

BACKGROUND

Imaging systems are increasingly used in a number of applications. These include remote sensing, medicine and manufacturing, including semiconductor fabrication, yield management and process diagnostics. One manner in which imaging systems are used is in comparing corresponding images. For example, a semiconductor wafer may include a number of substantially identical dies. An imaging system may capture corresponding images of two or more dies and compare the images to identify defects, differences, or irregularities. Imaging systems typically capture two dimensional attributes of selected attributes of three dimensional objects.

In order to compare the spatial location of objects represented in images, an imaging system first registers or correlates the corresponding images. This registration process may be described as an identification and alignment of a first image and a second, corresponding image, to account for any shift between the respective images. The registration step is important for making a meaningful comparison of the corresponding images. If the corresponding images are misaligned, the comparison of the images will be effected negatively. One method for performing this alignment is known as feature-based registration. As its name suggests, feature-based registration includes identifying geometric features on each image, establishing correspondence, and using the coordinates of these features to identify corresponding points on a corresponding image.

However, feature-based registration has significant disadvantages. Primarily, feature-based registration techniques are time consuming and require significant computational resources. In application, common features may become difficult to extract in the presence of noise, often leading to reliability issues. Further, in some applications it is desirable to rapidly register a plurality of corresponding pairs of complex images. Accordingly, a lengthy registration process, such as that associated with feature-based registration, limits the overall operational speed and throughput of the imaging system. Additionally, as the size of devices formed on semiconductor dies decreases, imaging system will be required to inspect increasingly small structures. As such, errors made in the registration of corresponding images will be amplified.

SUMMARY

Therefore, a need has arisen for an image registration system and method that is computationally efficient.

A further need has arisen for an image registration system and method that efficiently processes complex image data.

A still further need has arisen for an image registration method and system that facilitates increased system throughput.

A further need has arisen for an image registration system that is both accurate and robust.

In accordance with teachings of the present disclosure, a system and method are described for an image registration system and method that reduces disadvantages associated with previously used image registration systems. The image registration system of the present invention includes a registration engine that receives complex image data, such as frequency domain data, for corresponding images. The registration engine calculates an inverse of the complex conjugate product of the fast Fourier transform [FFT] of the complex image data of the first image and the FFT of the second, corresponding, image.

In one aspect of the present invention, an imaging system is disclosed that includes a positioning system, and optical system and a registration system. The positioning system may hold and selectively position a target such as a semiconductor wafer. An optical system is located proximate the positioning system and captures complex images of the target. The registration system connects to the imaging system and receives complex object wave data for pairs of corresponding images. The registration system then calculates a correlation map for each pair of images. The correlation data calculation includes calculating the inverse of a complex conjugate product of the FFT of the first image and the FFT of the second image.

More particularly, the imaging system may include a charge coupled device (CCD) camera for capturing holographic images of the target held by the positioning system. Further, the complex object wave data received by the registration engine may include phase data and magnitude data, complex spectrum data, or frequency data generally obtained from height and reflectance data for each point of the target. The imaging system may further include a comparison engine that compares the first image and the second, corresponding, image and can identify magnitude and phase differences between the first image and the second image.

In another aspect of the present invention, a method of registering image data of corresponding images is disclosed. The method includes receiving complex image data of a first image and a second image. The images may be in the form of frequency data and they may be subsequently filtered by a bandpass filer. The method further includes generating image registration data by calculating the inverse of the complex conjugate product of the FFT of the first image and the FFT of the second image. The method further includes finding the correlation peak by calculating the magnitude of complex correlation and searching for the maximum on the correlation magnitude map. The distance between the peak and the image center is found to be the translation or shift between the image pair.

The present invention provides a number of important technical advantages. One technical advantage is incorporating frequency domain techniques to generate registration data. The use of frequency domain data decreases computation requirements by making correlation calculations within the frequency domain, which minimizes computational costs in searching for a correlation peak between the images, in comparison to iterative techniques. The use of frequency domain data further supports the efficient processing of complex image data and increases imaging system throughput. Further the use of complex image data, including height and reflectance data for each point, X and Y, on the target, allows the system to be particularly accurate. The use of complex image data for registration also allows the system to be more robust than other registration systems.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Preferred embodiments and their advantages are best understood by reference to FIGS. 1 through 4 wherein like numbers are used to indicate like and corresponding parts.

Figure 1:
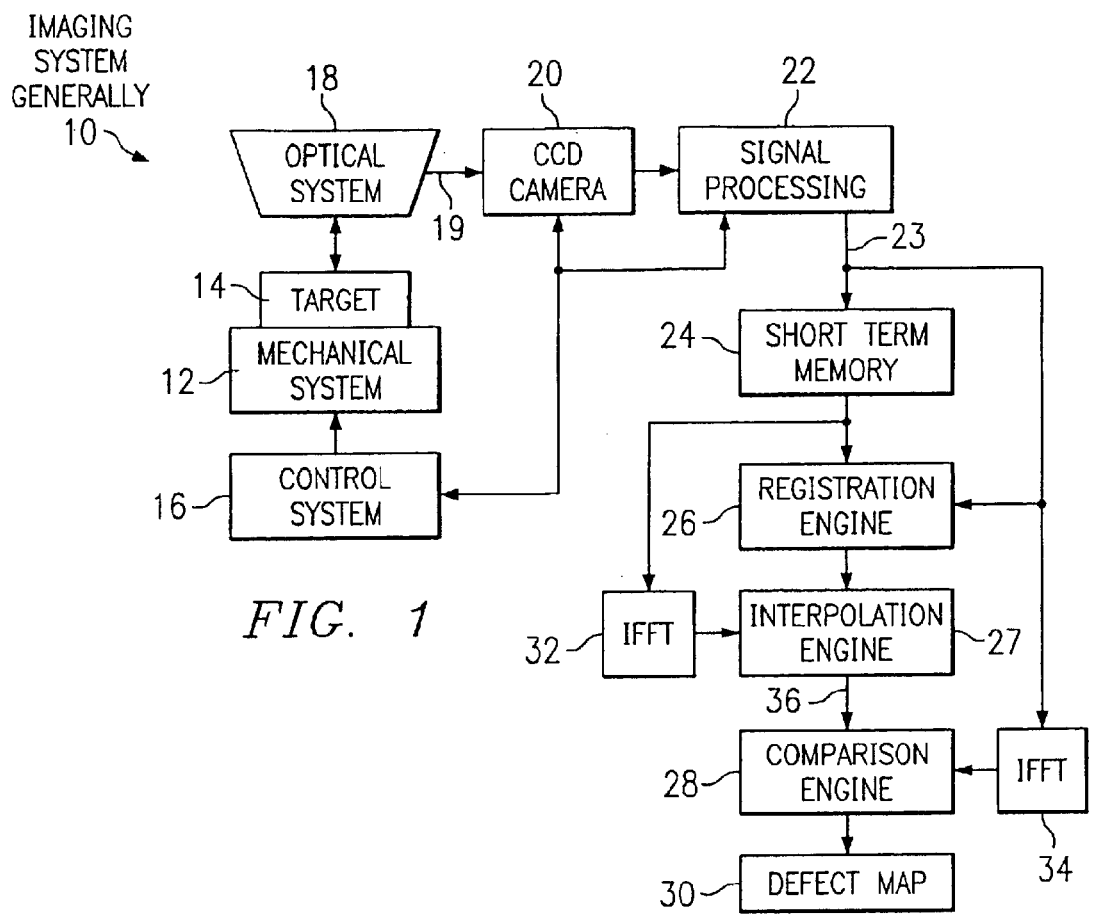
FIG. 1 depicts an imaging system according to the present invention.

Now referring to FIG. 1, an imaging system depicted generally at 10 according to the present invention is shown. Imaging system 10 includes mechanical system 12 operable to hold and position target 14. Target 14 may include a semiconductor wafer or another target suitable for inspection. Mechanical system 12 is preferably operable to selectively hold target 14 and is also operable to selectively position or 'step' target 14. In a preferred embodiment, mechanical system 12 is operable to selectively step target 14 in sequential steps sized according to the field view (FOV) of optical system 18. Optical system 18 is positioned proximate mechanical system 12 and target 14 such that optical system 18 may effectively capture images of target 14. Images captured by optical system 18 exit optical system 18 as spatial domain data 19. In a preferred embodiment, the image data captured by optical system include a measurement of height (z) and reflectance (a) for each position (x,y) of target 14. Accordingly, in this preferred embodiment, four dimensional spatial domain data is captured by optical system 18.

Mechanical system 12 is preferably operated by control system 14. Control system 14 is also preferably linked to CCD Camera 20 and signal processing system 22 and is operable to submit image location data thereto. Such image location data may be included with the captured image data to discern which images correlate to one another.

In the present embodiment, charged coupled device (CCD) camera 20 is further operably connected to optical system 18. In an alternative embodiment, any suitable device may be utilized to receive and store spatial domain data 19 from optical system 18. Optical system 18 and CCD camera 20 may preferably utilize direct to digital holography (DDH) techniques as shown in U.S. Pat. No. 6,078,392 issued to Clarence E. Thomas, et al. and incorporated herein by reference. Alternatively, optical system 18 and camera 20 may utilize any suitable technique to capture height (Z) and reflectance (A) data for points X,Y on target 14. In the present disclosure, reference to complex image data preferably includes image data that is derived from X,Y,Z and A obtained for portions of a given target. Complex data may preferably include X,Y,Z and A image data that has been transformed from the spatial domain into the frequency domain. In one particular embodiment, this transform may be accomplished using Fast Fourier Transform (FFT) techniques. X,Y,Z and A image data that has been transformed into frequency domain data, is referred to herein as frequency data or complex frequency data.

Light from optical system 18 may preferably be directed to CCD camera 20. CCD camera is operable to record holographic image data without the use of a photographic plates or film. Further, CCD camera 20 is preferably operable to digitally record the holographic image data captured by imaging system 10.

Signal processing system 22 is operably coupled to CCD camera 20. Signal processing system 22 is further operable to receive and process digital images from CCD camera 20. Processing by signal processing system 22 preferably includes transforming data recorded by camera 20 into frequency domain data. Preferably, this processing includes a Fourier transform of holographic data, locating the signal carrier frequency of the holographic data, and extracting the frequency of the complex object wave of the holographic data. The information extracted by signal processing system 22 may be generally referred to as frequency data and may include any frequency data obtained by transforming the spatial domain data received, into frequency domain data. In a particular embodiment, signal processing system 22 is operable to output Fast Fourier Transform (FFT) data in a streaming fashion with every instance representing the FFT of one field of view. Data processed by the signal processing system 22 may be sent to short term memory 24 and later sent to registration engine 26 when its corresponding field of view becomes available. Short term memory 24 may include any short term memory suitable for storing complex frequency data received from signal processing system 22. Short term memory 24 is further operatively connected to registration engine 26. When a new FOV comes out of signal processing 22, short term memory 24 is searched to find the frequency image of its corresponding FOV, previously captured. The frequency data of the image pair is then sent to registration engine 26. The new FOV data is then stored in short term memory 24 to wait for its corresponding FOV from the next die or corresponding target portion. The 'old' FOV data is removed from short term memory 24.

Registration engine 26 is operatively connected to signal processing system 22 as well as short term memory 24. Registration engine 26 is preferably operable to receive complex image data from signal processing system 22 and its corresponding complex image data from short term memory 24. Control system 16 is coupled to mechanical system 12 and is operable to control mechanical system 12. Control system 16 is further operable to control CCD camera 20 and signal processing system 22. Registration engine 26 is operable to identify the translation or 'shift' between the corresponding images. Translation identified by registration engine 26 may be shifts required in both the X and Y directions for one image to align with its corresponding image.

Interpolation engine 27 is operatively connected to registration engine 26 and short term memory 24 via an inverse transform. Interpolation engine 27 is further operable to resample the complex image received from short term memory 24 via an inverse transform such as an inverse Fast Fourier Transform (IFFT). This transform preferably transforms the data from the frequency domain to the spatial domain.

Interpolation engine 27 is preferably coupled to comparison engine 28. Comparison engine 28 is operable to receive corresponding images, one from signal processing system 22 via an inverse FFT and another from interpolation engine 27. Comparison engine 28 is further operable to compare corresponding images. The comparison made by comparison engine 28 includes complex image normalization, change vector computation, and thresholding.

Comparison engine 28 is operatively coupled to defect mapping engine 30. Defect mapping engine 30 preferably identifies defects, differences, or irregularities between the first image and the second corresponding image based upon the comparison results received from comparison engine 28 and registration engine 26.

Figure 2:
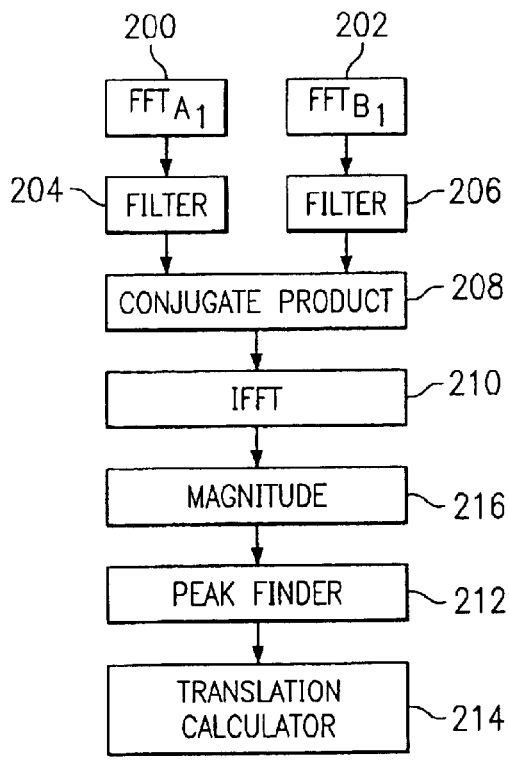
FIG. 2 is a flow diagram showing an image registration method according to the present invention.

Now referring to FIG. 2, a flow diagram of an image registration system, according to the present invention is shown. The image registration provides a frequency domain based correlator for the correlation of two complex signals in the spatial domain to be implemented in the frequency domain using the inverse Fourier transform of the product of their Fourier transforms, or a similar transform technique. The image registration system can be implemented using FFTs instead of a defined correlation measure in the spatial domain. The information contained in the frequency domain representation of the complete object wave includes phase data representing target height information that is not present in traditional frequency domain representations of magnitude reflectance images. Searching for the correlation peak can then be performed in the resultant correlation map.

Figure 4:
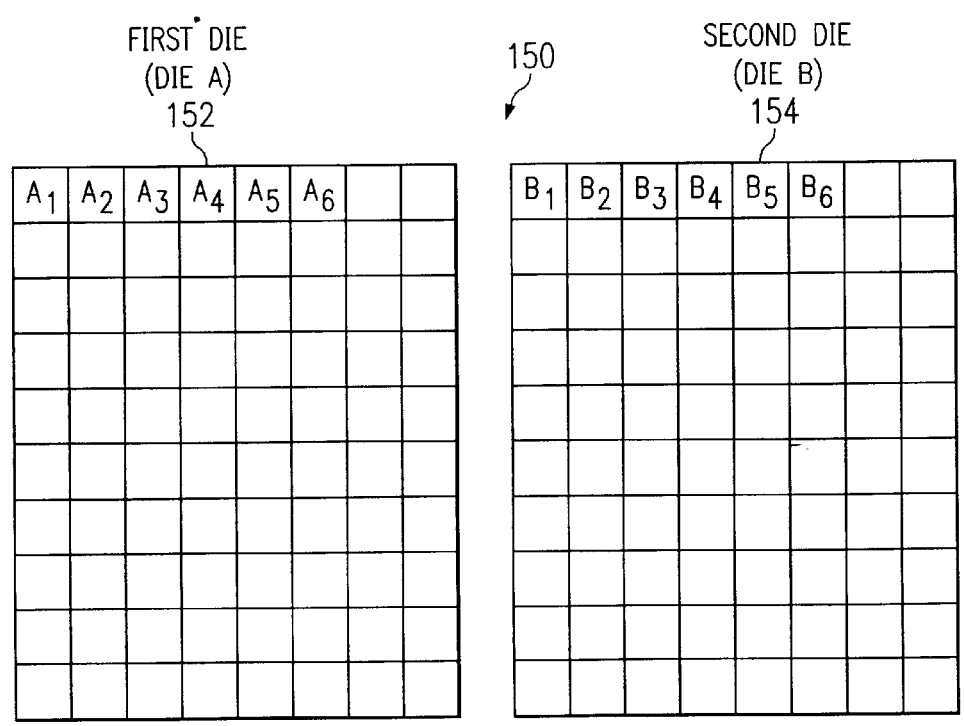
FIG. 4 depicts two corresponding semiconductor dies partitioned into multiple corresponding fields of view.

The method begins with identifying two corresponding image data, 200 and 202 from a first image and a second, corresponding, image. In the present embodiment, image data 200 and 202 may include frequency data of die portions A1 and B1 (as shown in FIG. 4). In a preferred embodiment, image data 200 and 202 are FFTs of the image data. The registration includes an initially filtering the FFT of the first data 204 and filtering the FFT of the second image data 206. In a preferred embodiment these filtering steps 204 and 206 utilize a bandpass filter, although any suitable filter for eliminating low frequency and high frequency noise may be employed. In a particular embodiment, filtering steps 204 and 206 preferably filter portions of the frequency that are below approximately fifteen (15) to twenty (20) percent of nyquist and above approximately sixty (60) percent of nyquist.

Next, the complex conjugate product of FFT A1 and FFT B1 is determined 208. The inverse FFT of the complex conjugate product is then calculated 210. Following this step, the magnitude of correlation is determined by calculating the magnitude of the inverse FFT 216. Finally, one peak is identified within the correlation magnitude data 212. The peak finding may preferably include parabolic interpolation techniques to identify peaks with sub-pixel accuracy. For example, for a 3×3 block of cross correlation results around the discrete peak values, this may include fitting those results with a three dimensional surface such as a parabola. The peak of the fitted surface is defined as the peak of correlation.

The identified peak is used to calculate the translation between the corresponding image pair 214. The translation is defined as the distance between the peak and the image center. The registration process above may preferably be repeated for a plurality of corresponding images.

After registration, a misregistration analysis and quality assurance check may be performed to determine whether an accurate registration has taken place and whether additional processing is needed to assure a desired registration accuracy. In one embodiment this process may include identifying the peak pattern of the correlation map and using the drop off between the first peak and the second peak to measure gauge the quality of the translation.

Additionally, image resampling and interpolation may be performed after the translation is determined. The translation defines a new grid for the target image. Resampling may then performed on the complex target image using an interpolator such as Bilinear or Sinc interpolation. After the target image has been resampled by interpolation engine 27, image comparison engine 28 may compare the complex image pair and identify differences between the first image and the second image.

Figure 3:
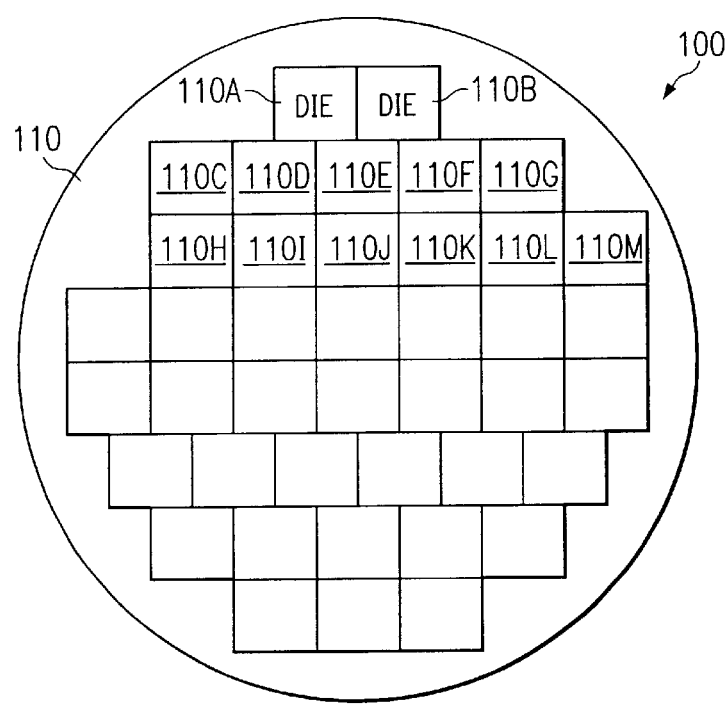
FIG. 3 shows a semiconductor wafer having multiple dies formed thereon.

Now referring to FIG. 3 is a demonstrative representation of a semiconductor wafer, indicated generally at 100, provided to describe the operation of the image registration system of the present invention. Wafer 100 includes a plurality of substantially identical dies 110 formed thereon. For descriptive purposes, dies 110 have been further labeled as 110A, 110B, 110C, etc. It should be understood that the present invention contemplates the registration of corresponding image data from corresponding dies, regardless of their arrangement upon one or more wafers.

Now referring to FIG. 4, which shows a demonstrative representation of corresponding dies, separated into a plurality of sections. First Die 152, or Die A includes a plurality of sections labeled A1, A2, A3, etc. Second Die 154 similarly includes a plurality of corresponding sections labeled B1, B2, B3 etc. In the present embodiment, die section A1 corresponds to die section B1. Die section A2 corresponds to die section B2, etc. The size of each die section is preferably substantially equal to the field of view (FOV) of optical system 18, as shown in FIG. 1. The size image of the die sections, or blocks is determined by FOV of optical system 18 and the spatial resolution of CCD camera 20, as shown in FIG. 1.

In operation, mechanical system 12 preferably positions target 14 such that a preferred portion of a target, such as dies section A1, is positioned in the field of view of optical system 18. Optical system 18 may then obtain image data such as the complete object wave of holographic image data.

Image data captured by optical system 18 may then preferably be sent to CCD camera 20, as described in FIG. 1. After the image of die section A1 is captured by optical system 18, mechanical system 12 may then move or 'step' the wafer such that a different die section, such as die section A2, are positioned in the field of view of the optical system 18. Accordingly, each 'step' of mechanical system 12 is preferably sized according to the field of view of optical system 18. In a preferred embodiment, the movement of mechanical system 12 follows a preselected pattern to ensure that all areas of interest on target 12 are properly imaged. In an alternative embodiment, a mechanical system may position an optical system with respect to a fixed target. In another alternative embodiment, mechanical system 12 may continuously move target 14 through the field of view of optical system 18 and optical system 12 capture images at selected time intervals to ensure that the areas of interest of target 12 are properly imaged.

Image data is sent from optical system 18 to CCD camera 20 and then to signal processing system 22. The processed image data sent on to be registered may be in any suitable format such as: the raw frequency domain signal after carrier frequency is extracted, the complex spatial domain data, the magnitude image data, and the phase data. This capability of being able to process image data in a variety of formats may alleviate data processing or pre-processing requirements. Alternatively, data suitable for registration may be obtained from any point along the data stream in which suitable complex image data may be obtained.

The processed image data may then be both held in short term memory 24 and sent directly to registration engine 26. Registration engine 26 identifies which images are associated with corresponding die portions by identifying the position of an image in a wafer coordinate system. In a preferred embodiment this may be accomplished by identifying the die number and the frame coordinates within the die for each image, as determined by control system 16, as shown in FIG. 1.

Although the disclosed embodiments have been described in detail, it should be understood that various changes, substitutions and alterations can be made to the embodiments without departing from their spirit and scope.

What is claimed is:

1. An imaging system comprising:

a positioning system operable to position a target;

an optical system disposed proximate the positioning system and operable to capture a holographic image of the target;

a charged coupled device (CCD) camera operatively coupled with the optical system and operable to digitally record the holographic image data captured by the optical system, the holographic image data comprising a complete object wave, wherein the complete object wave comprises: phase data representing the target height and reflectance data for points X and Y on the target;

a registration system operatively coupled to the optical system and operable to:

receive frequency data for a first image and a second corresponding image, the frequency data corresponding to the complete object wave data recorded by the CCD camera; and calculate correlation data for the first image and the second image, the correlation data comprising an inverse transform of a complex conjugate product of the frequency data of the first image and the frequency data of the second image, the correlation data comprising a correlation translation between the first image and the second image.

2. The imaging system of claim 1 wherein the frequency data further comprises a FFT of the complete object wave data.

3. The imaging system of claim 1 wherein:

the first image further comprises an image of a portion of a first die; and the second image further comprises an image of a corresponding portion of a second die.

4. The imaging system of claim 1 further comprising the registration engine operable to:

receive the FFT of the first image;

receive the FFT of the second image; and determine the conjugate product of the FFT of the first image and the FFT of the second image.

5. The imaging system of claim 1 further comprising the registration engine operable to:

receive complete object wave data for a plurality of corresponding images; and output correlation data for the plurality of corresponding images.

6. The imaging system of claim 1 further comprising the comparison engine operable to:

compare the first image and the second image; and identify phase differences between the first image and the second image.

7. An image registration system comprising:

a registration engine operable to:

receive complete object wave data for corresponding image pairs, wherein the complete object wave data comprises: phase data representing the target height and reflectance data for points X and Y on a target and; the image pairs having a first image and a second corresponding image; and calculating an inverse transform of a complex conjugate of the fast Fourier transform of the first image and the fast Fourier transform of the second image.

8. The image registration system of claim 7 wherein the complete object wave data of the first image and the second image further comprise complete object wave data captured by a CCD camera.

9. The image registration system of claim 7 further comprising the registration engine operable to filter the complete wave data.

10. The image registration system of claim 7 wherein:

the first image further comprises an image of a portion of a first die; and the second image further comprising an image of a corresponding portion of a second die.

11. The image registration system of claim 7 further comprising the registration engine operable to:

receive the FFT of the first image;

receive the FFT of the second image;

determine the conjugate product of the FFT of the first image and the FFT of the second image.

12. The image registration system of claim 7 further operable to determine a correlation map between the first image and the second image.

13. The image registration system of claim 7 further operable to register a plurality of complex image pairs.

14. A method of registering image data of correlated images comprising:

receiving complex image data of a first image comprising a first complete object wave, wherein the first complete object wave comprises: phase data representing a target height and reflectance data for points X and Y on the target;

receiving complex image data of a second image, the second image corresponding to the first image and comprising a second complete object wave;

calculating the inverse of the complex conjugate product of the fast Fourier transform of the first image and the fast Fourier transform of the second image; and calculating a correlation magnitude utilizing the inverse complex conjugate product.

15. The method of claim 14 further comprising identifying a translation of the first image with respect to the second from the correlation magnitude map.

16. The method of claim 14 further comprising registering image data from a plurality of correlated images.

17. The method of claim 14 further comprising:

identifying a plurality of control points based upon the inverse complex conjugate product; and performing a misregistration analysis based upon a peak pattern identified on a correlation map.

* * * * *